(12) United States Patent
Zuo

(10) Patent No.: US 7,969,575 B2
(45) Date of Patent: Jun. 28, 2011

(54) METHOD AND APPARATUS FOR MEASURING LIGHT ABSORPTION OF LIQUID SAMPLES

(75) Inventor: Peter Du-hai Zuo, Fremont, CA (US)

(73) Assignee: Quawell Technology, Inc., Sunnyvale, CA (US)

( * ) Notice: Subject to any disclaimer, the term of this patent is extended or adjusted under 35 U.S.C. 154(b) by 324 days.

(21) Appl. No.: 12/364,943

(22) Filed: Feb. 3, 2009

(65) Prior Publication Data

US 2010/0195098 A1 Aug. 5, 2010

(51) Int. Cl.
*G01N 21/00* (2006.01)
(52) U.S. Cl. ....................................... 356/432
(58) Field of Classification Search ........... 356/432–444
See application file for complete search history.

(56) References Cited

U.S. PATENT DOCUMENTS

| | | | | |
|---|---|---|---|---|
| 5,275,159 | A * | 1/1994 | Griebel | 600/324 |
| 6,549,275 | B1 * | 4/2003 | Cabuz et al. | 356/39 |
| 6,628,382 | B2 | 9/2003 | Robertson | |
| 6,809,826 | B2 * | 10/2004 | Robertson | 356/440 |
| 7,397,036 | B2 * | 7/2008 | Robertson et al. | 250/368 |
| 2006/0198761 | A1 | 9/2006 | Tokhtuev et al. | |
| 2006/0281094 | A1 | 12/2006 | Squirrell et al. | |
| 2007/0285645 | A1 | 12/2007 | Schwertner et al. | |

FOREIGN PATENT DOCUMENTS

WO 00/25133 A1 5/2000

OTHER PUBLICATIONS

International Search Report and Written Opinion mailed Mar. 23, 2010, for International Application No. PCT/US2010/022125, filed Jan. 26, 2010, 9 pages.

* cited by examiner

*Primary Examiner* — Gregory J. Toatley, Jr.
*Assistant Examiner* — Jarreas C Underwood
(74) *Attorney, Agent, or Firm* — Blakely Sokoloff Taylor & Zafman LLP

(57) ABSTRACT

Techniques for measuring light absorption of liquid samples are described herein. According to one embodiment, an apparatus includes an upper arm having a first measuring surface and a lower arm having a second measuring surface coupled to the lower arm via a hinge. The upper arm is capable of swinging via the hinge. One of the measuring surfaces is coupled to a light source while the other is coupled to a detector. The apparatus further includes an actuator configured to position the upper arm into a first measuring position. The first measuring surface of the upper arm and the second measuring surface of the lower arm are spaced approximately to contact and sandwich a liquid sample in between to form an optical path, such that light generated from the light source is received and detected through the light path by the detector for measuring light absorption by the liquid sample. Other methods and apparatuses are also described.

20 Claims, 17 Drawing Sheets

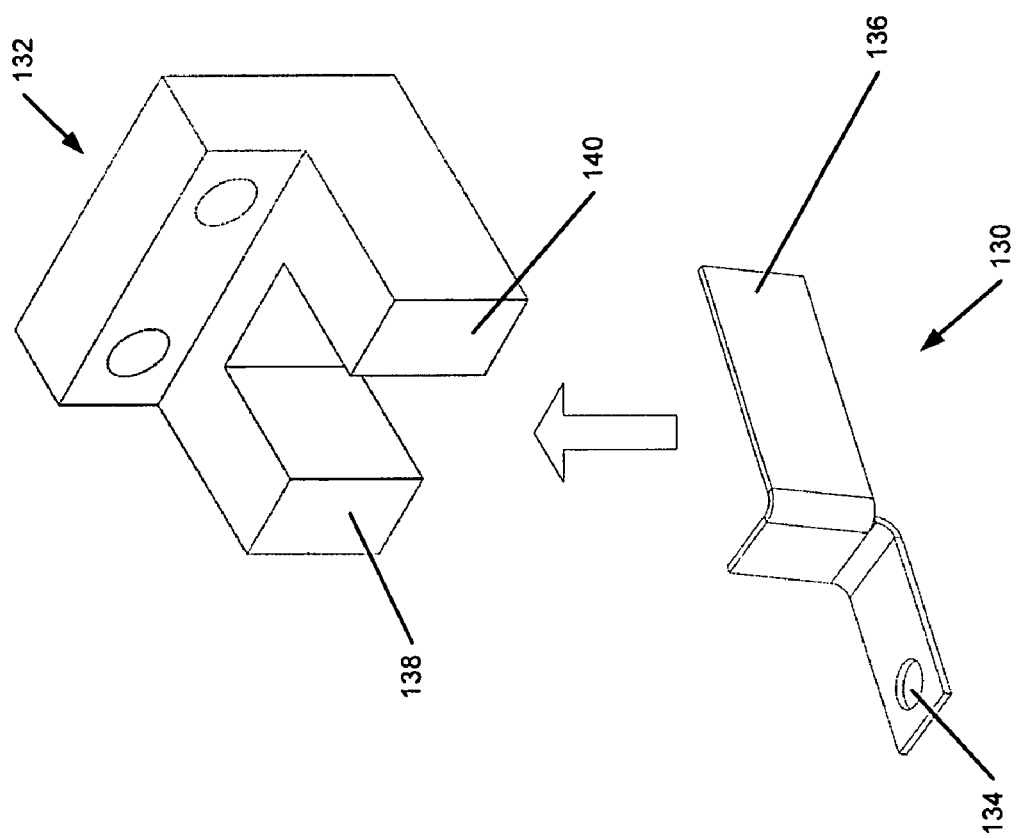

METHOD AND APPARATUS FOR MEASURING LIGHT ABSORPTION OF LIQUID SAMPLES

FIELD OF THE INVENTION

The present invention relates generally to liquid photometers. More particularly, this invention relates to measuring light absorption of liquid samples.

BACKGROUND

There is a need to measure the purity of fluids in many different circumstances. Devices used for measuring fluid purity in general, and for identifying and quantifying the amount of impurities in particular, commonly use light as a probing mechanism. Such devices are generally referred to as photometers. A specific type of photometer is the spectrophotometer, which permits adjustment of the light frequency (i.e., wavelength), for making measurements at multiple frequencies. The term "spectrophotometer" as used herein includes any photometer, including reflectometers, transmissometers, and nephelometers, adapted for this purpose.

Light that is used to irradiate material may either be reflected by the material, transmitted through the material, or absorbed by the material. Where the light is absorbed by the material, the material may also emit light in response, or fluoresce. In devices used to measure purity, one of three basic measurement methodologies following from these potential interactions of the light with the matter is generally employed. These methodologies measure the parameters absorption, reflectance, and fluorescence and are referred to herein as absorption, reflectance, and fluorescence methodologies. According to the various methodologies, a light detector is disposed with respect to a light transmitter so that the detector is optimally positioned to be responsive to the associated parameter.

However, there has been a lack of measuring mechanisms that can measure light absorption of liquid samples in a precision manner.

SUMMARY OF THE DESCRIPTION

Techniques for measuring light absorption of liquid samples are described herein. According to one embodiment, an apparatus includes an upper arm having a first measuring surface and a lower arm having a second measuring surface coupled to the lower arm via a hinge. The upper arm is capable of swinging via the hinge. One of the measuring surfaces is coupled to a light source while the other is coupled to a detector. The apparatus further includes an actuator configured to position the upper arm into a first measuring position. The first measuring surface of the upper arm and the second measuring surface of the lower arm are spaced approximately to contact and sandwich a liquid sample in between to form an optical path, such that light generated from the light source is received and detected through the light path by the detector for measuring light absorption by the liquid sample. Other methods and apparatuses are also described.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings in which like references indicate similar elements.

FIG. 5 shows a perspective view of an optical positioning sensing apparatus according to one embodiment of the invention.

DETAILED DESCRIPTION

Techniques for measuring light absorption of liquid samples are described herein. In the following description, numerous details are set forth to provide a more thorough explanation of embodiments of the present invention. It will be apparent, however, to one skilled in the art, that embodiments of the present invention may be practiced without these specific details. In other instances, well-known structures and devices are shown in block diagram form, rather than in detail, in order to avoid obscuring embodiments of the present invention.

Reference in the specification to "one embodiment" or "an embodiment" means that a particular feature, structure, or characteristic described in connection with the embodiment is included in at least one embodiment of the invention. The appearances of the phrase "in one embodiment" in various places in the specification do not necessarily all refer to the same embodiment.

According to certain embodiments, a liquid sample measuring device includes an upper arm coupled a fixed arm (also referred to as a lower arm) via a hinge. The upper arm can be swung or rotated relatively to the fixed arm via the hinge. Each of the upper arm and fixed arm includes a measuring platform attached thereon. Each of the measuring platforms includes a measuring surface for containing a liquid sample to be measured or tested. The device further includes an actuator having a step motor to position the upper arm in multiple measuring positions in a precise manner by controlling a distance between the measuring surfaces of the upper arm and the fixed arm.

Figure 1A:
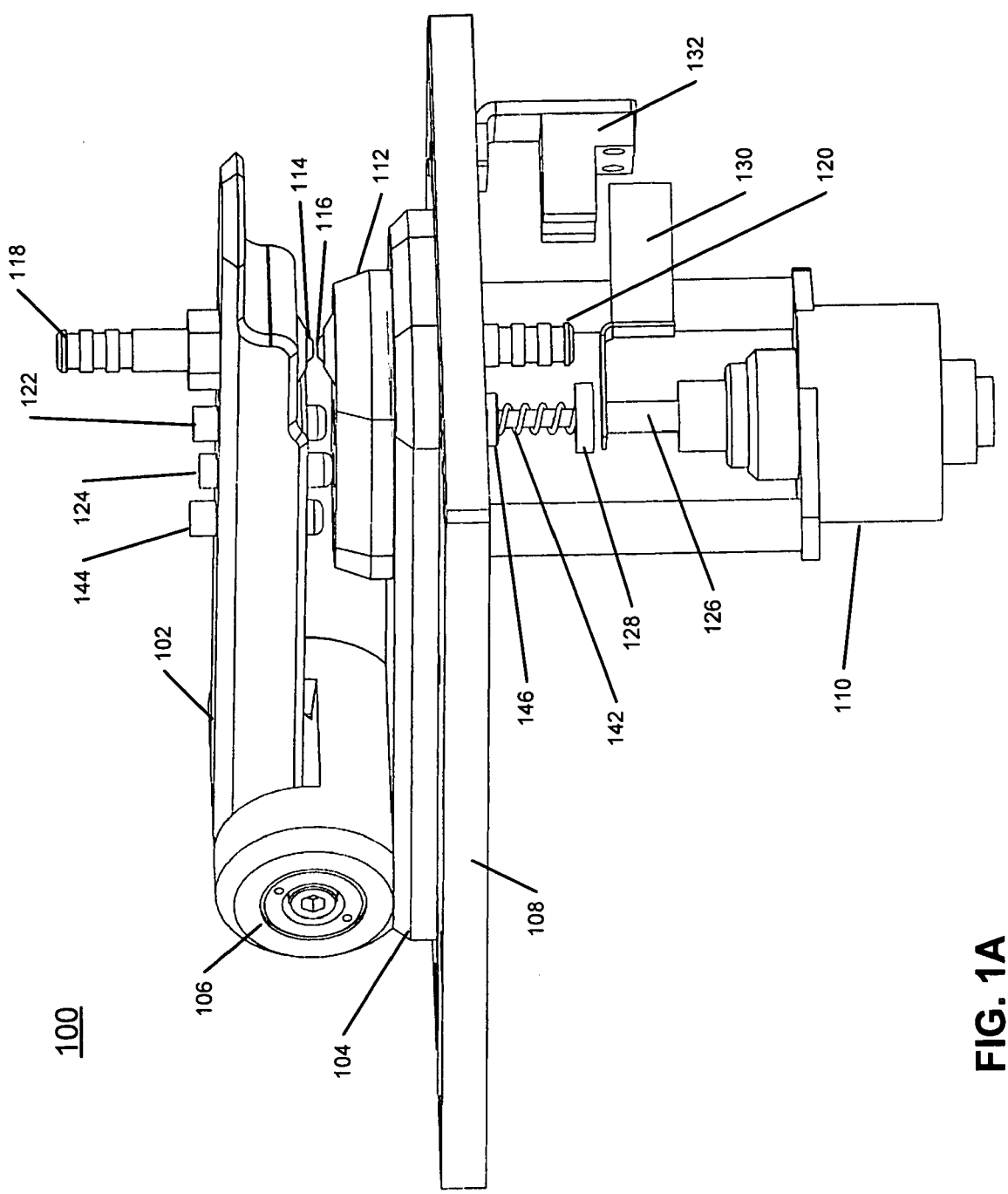
FIGS. 1A-1C show perspective views of an apparatus for measuring liquid sample according to one embodiment of the invention.
Figure 1B:
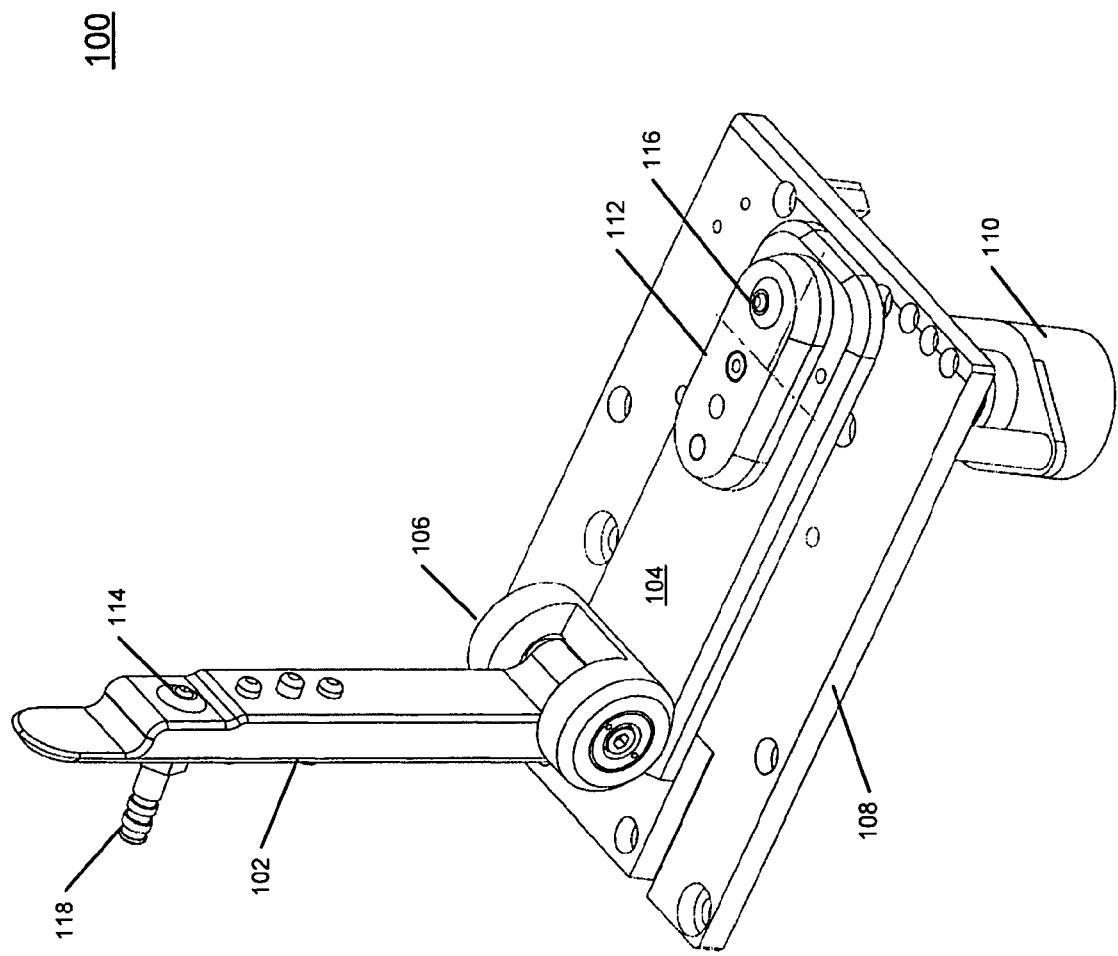
Figure 1C:
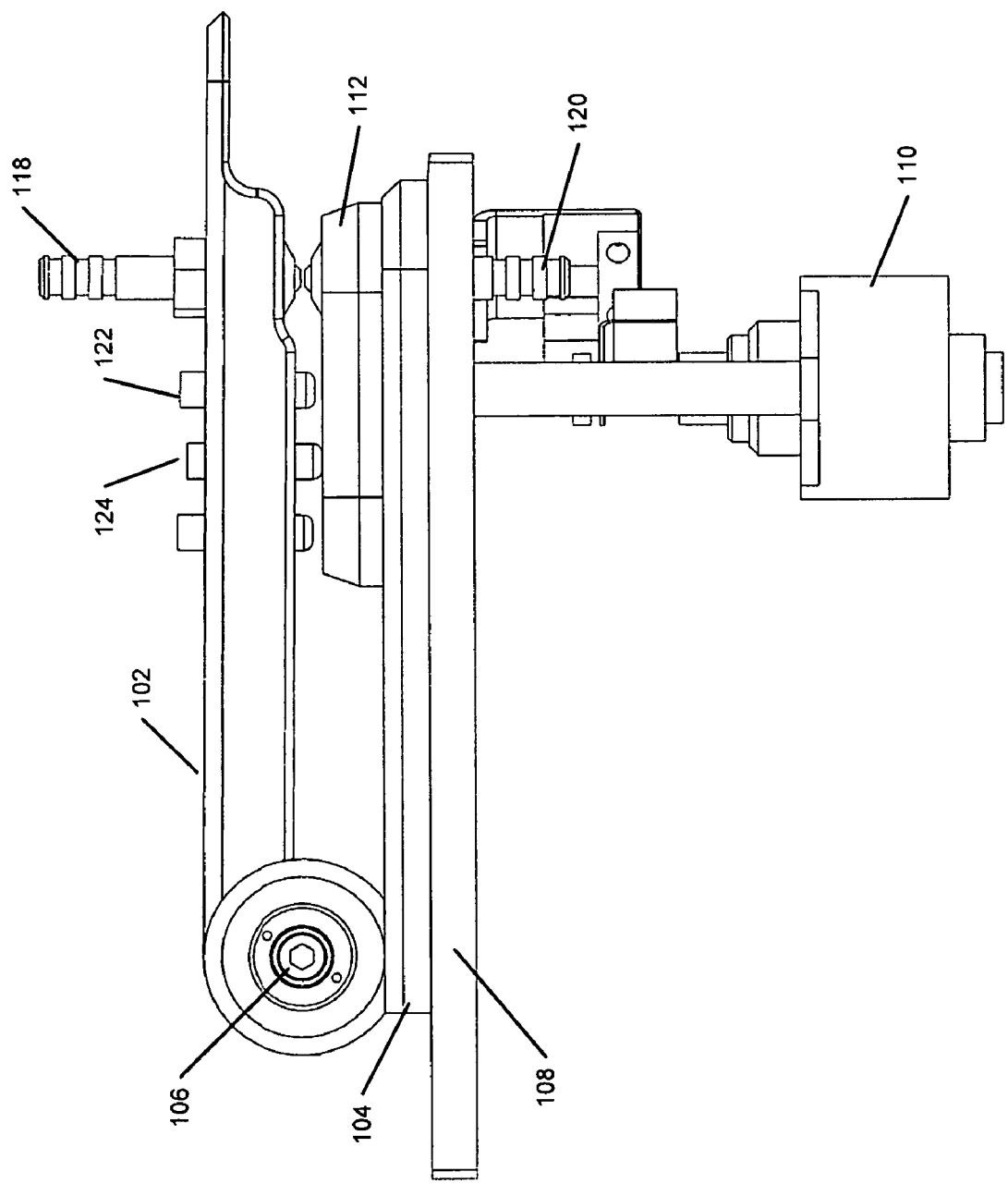

FIGS. 1A-1C show perspective views of a liquid sample measuring device according to one embodiment of the invention. Referring to FIGS. 1A-1C, according to one embodiment, device 100 includes an upper arm 102 coupled to a fixed or lower arm 104 via a hinge 106, where the upper arm 102 can be lifted or lowered by swinging or rotating the upper arm 102 via the hinge 106. The lower arm 104 is fixedly mounted on a baseboard 108.

In addition, according to one embodiment, measurement base platform 112 is mounted on the top of lowered arm 104. The upper arm 102 includes a measuring platform having a measuring surface 114 disposed thereon. Similarly, the lower arm 104 includes a measuring platform having a measuring surface 116 disposed thereon. When the upper arm 102 is lifted as shown in FIG. 1B, a liquid sample can be deposited onto the measuring surface 116 of the lower arm 104 using a pipette. The upper arm 102 can then be lowered and positioned, for example, by an actuator 110, into a measuring position as shown in FIG. 1C in which the liquid sample is in contact with (e.g., sandwiched) both the upper arm 102 and the lower arm 104. Characteristics of the liquid sample can be obtained by measuring absorption of light traveling through the liquid sample.

Further, the upper arm 102 further includes a fiber optic connector 118 mounted on a top surface of the upper arm 102. The fiber optic connector 118 can be any kind of fiber optic connectors, such as, in this example, a threaded coupler. Connector 118 can be coupled to an optical fiber which is coupled to a light source (not shown) that can emit and transmit light through the optical fiber. Fiber optic connector 118 includes a channel embedded therein (not shown) to allow the light to reach measuring surface 114. Similarly, lower arm 104 includes a fiber optic connector 120 mounted on a bottom surface of lower arm 104 through the baseboard 108. The fiber optic connectors 118 and 120 are aligned with each other such that light can travel through both connectors, forming an optical path. Fiber optic connector 120 includes a channel embedded therein (not shown) to allow the light to reach the optical fiber via measuring surface 114. The fiber optic connector 120 may be coupled to a measuring device to collect light traveling through the optical fiber for the purposes of measuring light absorption of the liquid sample.

When the upper arm 104 is positioned by actuator 110 to a measuring position, both measuring surfaces 114 and 116 are in contact with a liquid sample to be measured, where surfaces 114 and 116 are not directly in contact with each other. As a result, an optical path is formed from fiber optic connector 118 to fiber optic connector 120 via surfaces 114 and 116 sandwiching the liquid sample in between.

The spacing between surface 114 of upper arm 102 and surface 116 of lower arm 104 is controlled by pins 122 and 124 for a variety of measuring positions. The upper arm 102 is positioned lower or higher by actuator 110. Actuator 110 includes a step motor and a push rod 126, which when the step motor rotates, the pushing rod 126 is moved linearly up and down. The pushing rod 126 when extended upwardly pushes pushing pin 128 which in turn pushes pin 122 that pushes upper arm 102 upwardly. When the step motor rotates in a reversed direction, the pushing rod 126 is lowered and the upper arm 102 is lowered due to gravity. The step motor may be controlled by a computer program which may be stored in a machine storage medium and executed by a processor or controller.

According to one embodiment, device 100 further includes a U-shape positioning optical sensing piece 132 and a positioning optical blocking piece 130. The U-shape positioning optical sensing piece 132 is mounted underneath baseboard 108 and the positioning optical blocking piece 130 is mounted on the pushing rod 126 of actuator 110. One of the terminals of the U-shape piece 132 is equipped with a light or laser source (not shown) while the other terminal is equipped with an optical sensor (not shown) aligned with the light source of the opposing terminal. The optical sensor is coupled to a controller (not shown) which in turn controls the operations of actuator 110 based on signals received from the optical sensor (e.g., in response to receiving or not receiving light transmitted from the light source) mounted on the opposing terminal.

Figure 6D:
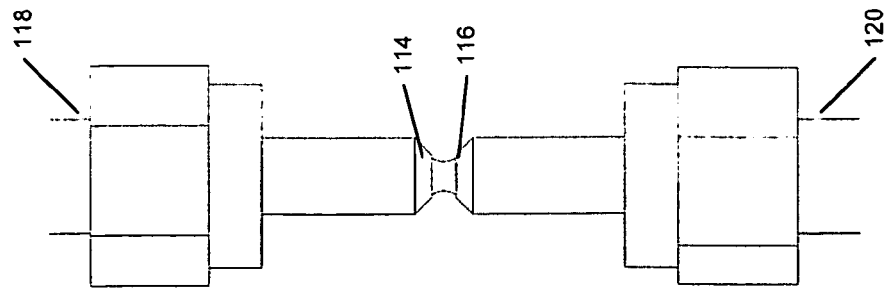
FIGS. 6A-6D show perspective views of measuring surfaces according to certain embodiments of the invention.
Figure 6C:
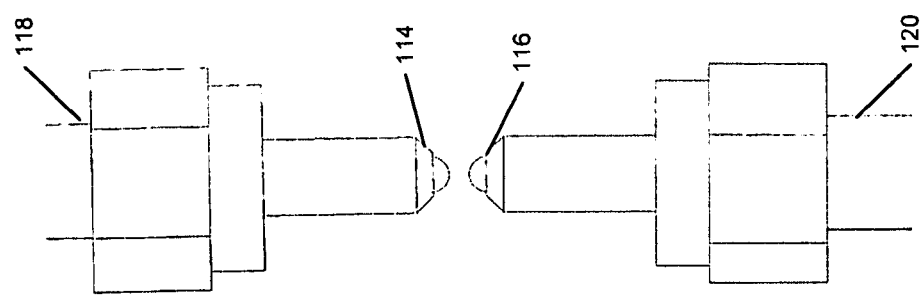
Figure 6B:
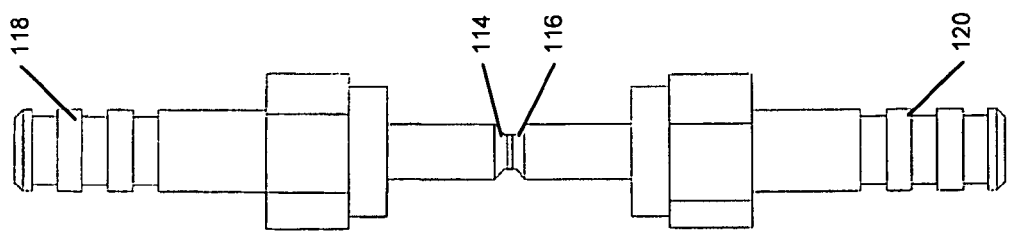
Figure 6A:
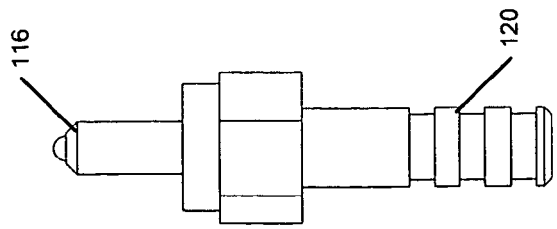

According to one embodiment, after a liquid sample to be measured has been deposited onto measuring surface 116 of lower arm 104, as shown in FIG. 6A, a user may lower the upper arm 102 which rests onto the lower arm 104 via pin 124 as shown in FIG. 1C, where the lower end of pin 124 rests against a top surface of lower arm 104. At this point, surface 114 of upper arm 102 and surface 116 of lower arm 104 are in contact with the liquid sample as shown in FIG. 6B.

Once the upper arm 102 has been lowered, a preprogrammed measuring procedure may be carried out by a processor or controller. Initially, actuator 110 is activated to position upper arm into a home or origin position. In one embodiment, actuator 110 is activated by moving pushing rod 126 upward which in turn pushes pushing pin 128 up. The pushing pin 128 in turn pushes the upper arm 102 by pushing pin 122 mounted within upper arm 102. Meanwhile, the optical blocking piece 130 is moved upwardly along with pushing rod 126.

As shown in FIG. 5, blocking piece 130 includes a first end 134 having an opening used to mount the blocking piece 130 onto pushing rod 126. Blocking piece 130 further includes a second end 136 twisted in approximately 90 degrees relative to the first end. When pushing rod 126 is pushed higher, the second end 136 of blocking piece is moved upwardly into an opening space between terminals 138 and 140 of U-shape sending piece 132, which blocks the light or laser transmitted from one terminal to the other. Once the light is blocked by the blocking piece 130, a signal is transmitted to a controller (not shown). In response to the signal, the controller may stops the actuator and mark the current position as a home or origin position, as shown in FIGS. 2A-2C.

In one embodiment, referring back to FIGS. 1A-1C, a spring is placed between a stop surface of pushing pin 128 and a plunger 146 inserted into base platform 112 through lower arm 104 and baseboard 108. In this embodiment, an elongate portion of the pushing pin 128 is inserted into an opening center of spring 142 and wrapped by the wire coil of spring 142. However, spring 142 is retained by the stop surface of pushing pin 128 as the diameter of stop surface is larger than the diameter of elongate portion of the pushing pin 128. As result, when the pushing rod 126 is pushed higher by the actuator 110, spring 142 is compressed between the stop surface of pushing pin 128 and the plunger. When the pushing rod 126 is lowered by the actuator 110, the compressed spring 142 is released which in turns pushes the pushing pin 128 lower. Furthermore, a metal piece 144 is inserted into and penetrated through upper arm 102 aligned with a magnet embedded within lower arm 104. As a result, due to the magnetic field generated between the magnet and metal piece 144, upper arm 102 is attracted (e.g., "pulled") towards to lower arm 104.

Figure 2A:
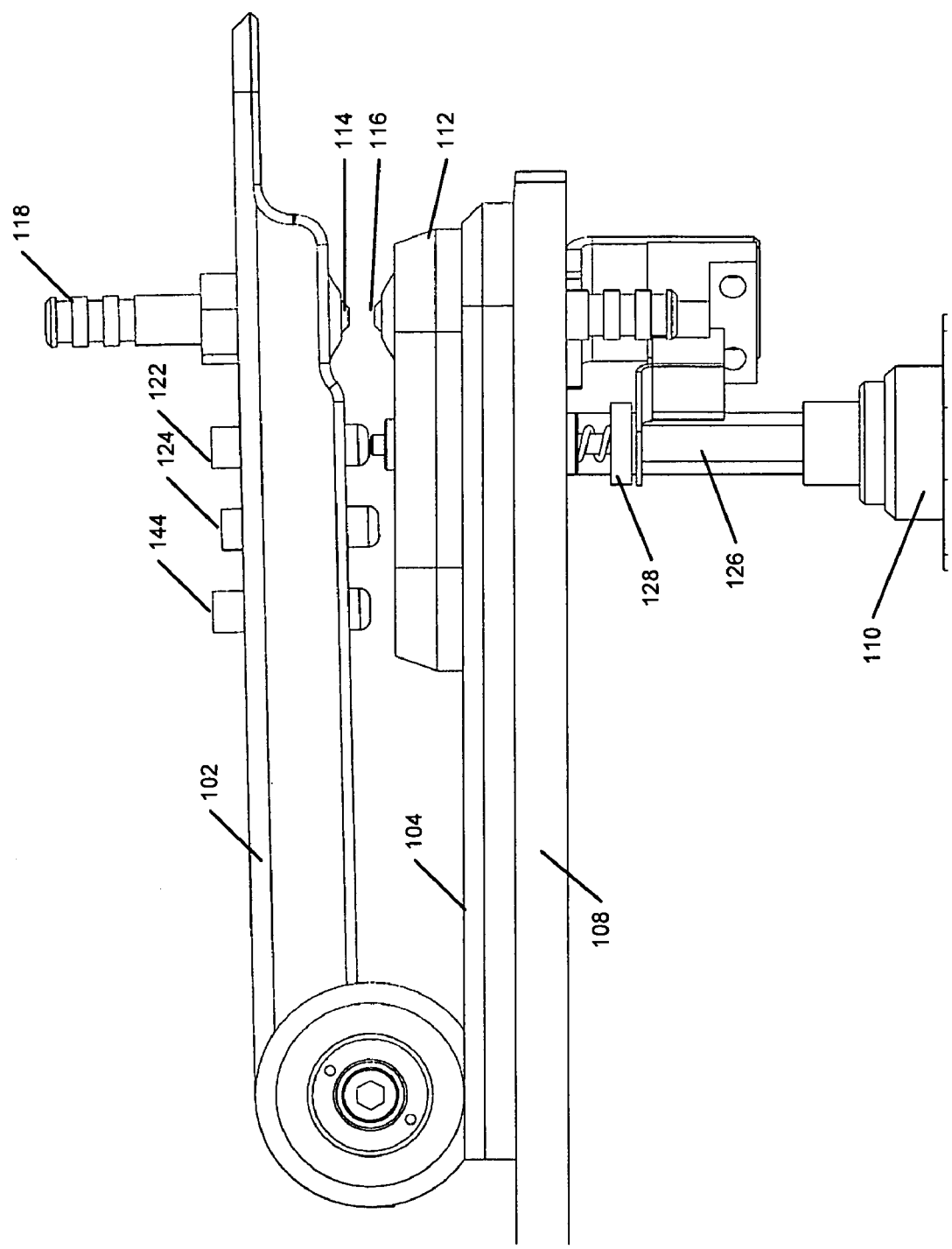
FIGS. 2A-2C show perspective views of an apparatus for measuring liquid sample according to one embodiment of the invention.
Figure 2B:
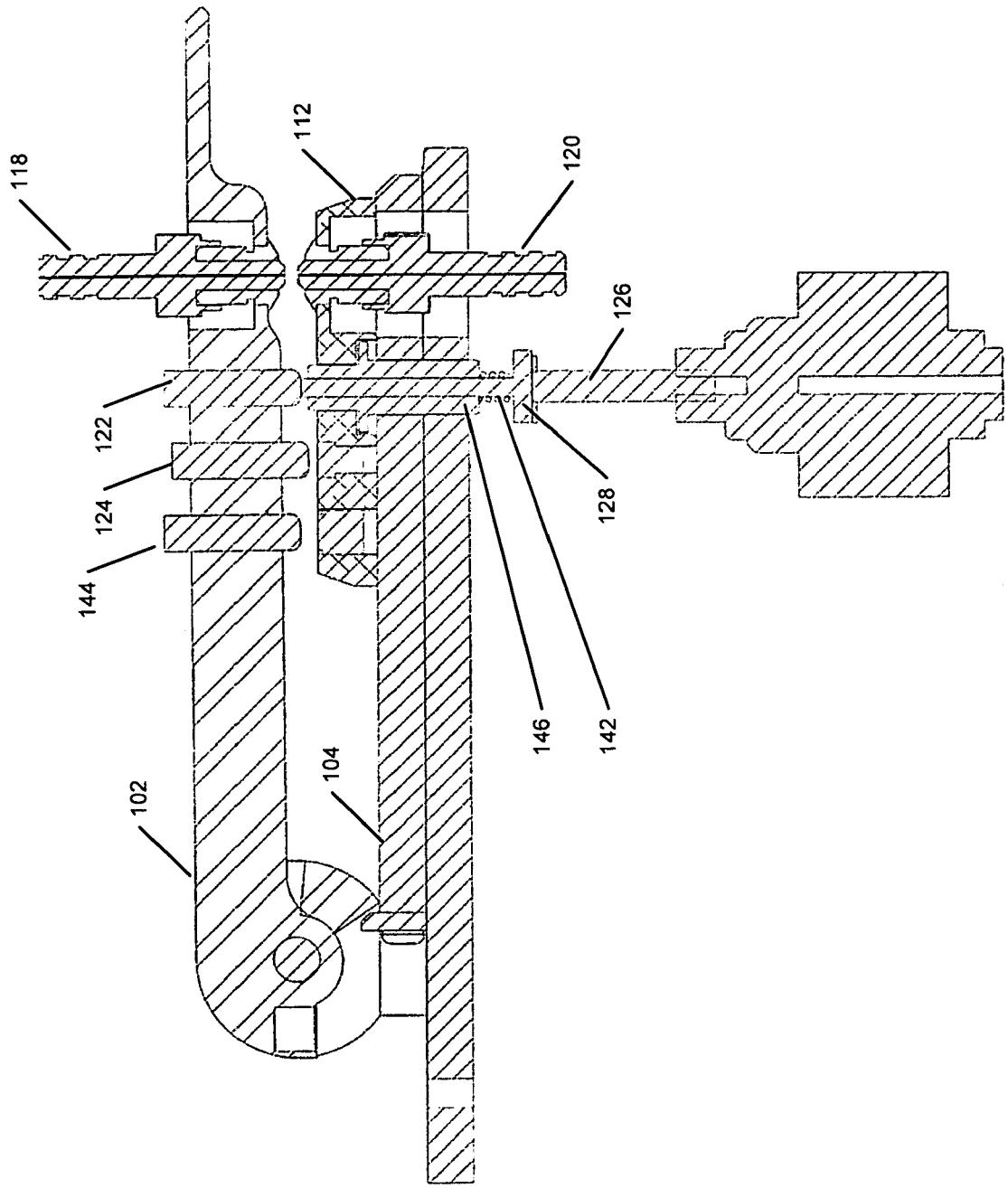
Figure 2C:
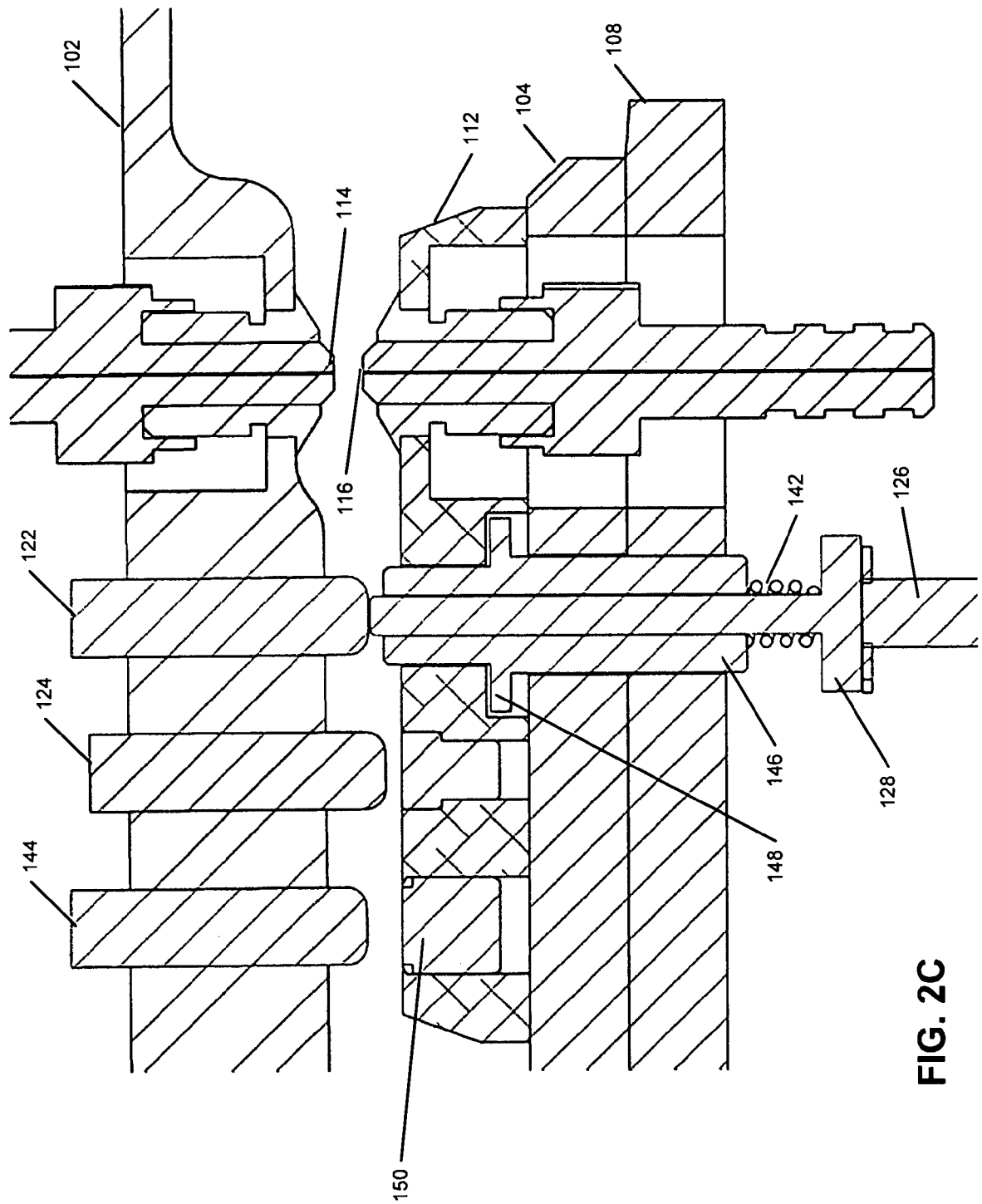

Now referring to FIGS. 2A-2C, according to one embodiment, plunger 146 includes a stopping ring 148 having a diameter larger than the diameter of an elongate portion of the plunger 146. Base platform 112 further includes a recess or cutout to contain or house the stopping ring 148 of plunger 146. When base platform 112 is mounted onto the top surface of lower arm 104 the cutout of base platform 112 and lower arm 104 form an internal room enclosing the stopping ring 148 of plunger 146 therein. The base platform 112 and lower arm 104 further include a sliding tunnel to allow plunger 146 to slide up and down. However, because of the stopping ring 148 contained by the internal room formed by base platform 112 and lower arm 104, the movement of plunger 146 is limited by a vertical space of the internal room enforced by the stopping ring 148 of plunger 146. Furthermore, plunger 146 includes a sliding tunnel to allow pushing pin 128 to slide up and down within plunger 146.

According to one embodiment, when pushing rod 126 is moving upwardly, it pushes the pushing pin 128 up. Meanwhile, spring 142 is compressed by the stop surface of the pushing pin 128. The compressed spring 142 in turn pushes plunger 146 up along with the pushing pin 128, until plunger 146 is stopped by a top inner wall (e.g., ceiling wall) of the internal room as shown in FIG. 2C. At this point, a top portion of plunger 146, as well as pushing pin 128, is moved up and exposed beyond a top surface of base platform 112, which in turn pushes upper arm 102 upwardly. Note that as described above, simultaneously, a positioning blocking piece 130 is moved up along with the pushing rod 126.

The pushing rod 126 is continuously pushed up even though plunger 146 has been stopped by the stopping ring 148, until the positioning blocking piece 130 enters and blocks the light or laser transmitted between terminals of the U-shape positioning sensing block 132 as described above. When pushing rod 126 finally stops in response to a signal generated by the U-shape positioning sensing block 132, the tip portion of pushing pin 128 has been pushed beyond the tip of plunger 146 which pushes upper arm 102 even further up. This position is referred to herein as a home or origin position. Note that the space between measuring surfaces 114 and 116 is determined by the position of pin 122 relative to the positions of plunger 146 and pushing pin 128, etc. At the home position, the space between measuring surfaces 114 and 116 is greater than 1 millimeter (mm), preferably around 2 mm, which may be adjustable dependent upon a specific configuration. At this point, the liquid sample is broken into two separate parts as shown in FIG. 6C transitioned from FIG. 6B. Due to molecular effects, one part is attached to measuring surface 114 and the other part is attached to measuring surface 116. Since two parts are separated, no optical path exists at this position.

Figure 3A:
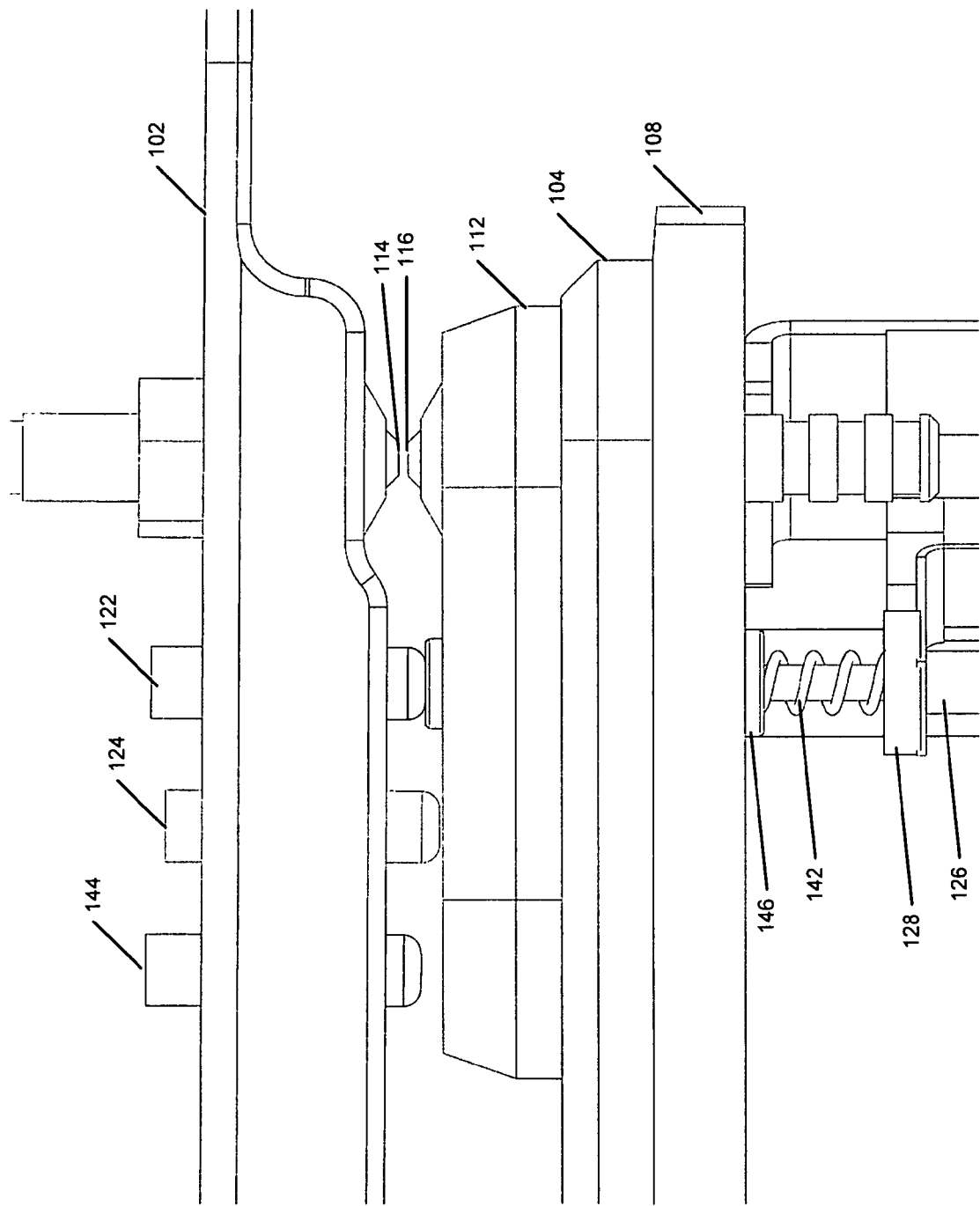
FIGS. 3A-3C show perspective views of an apparatus for measuring liquid sample according to one embodiment of the invention.
Figure 3B:
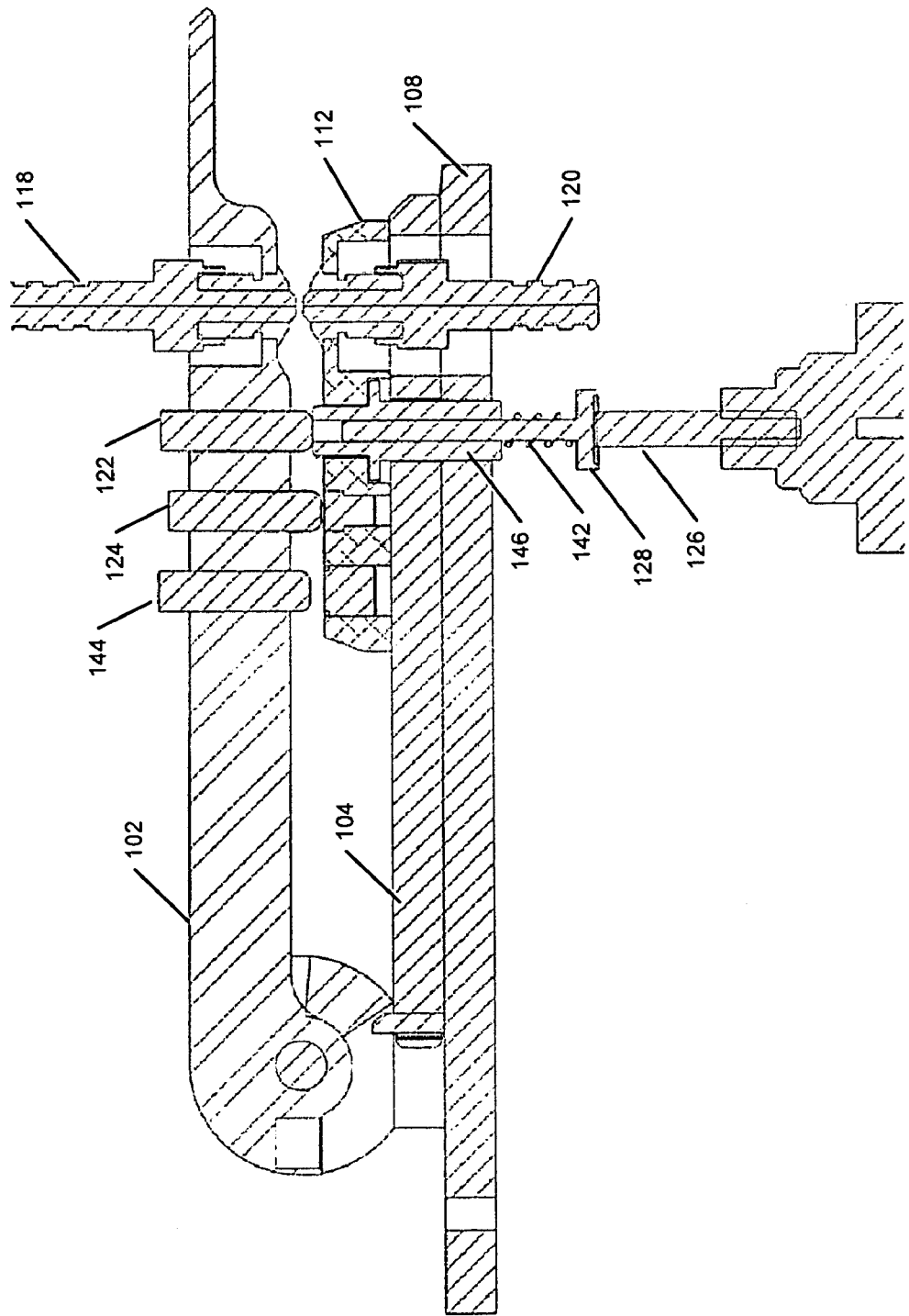
Figure 3C:
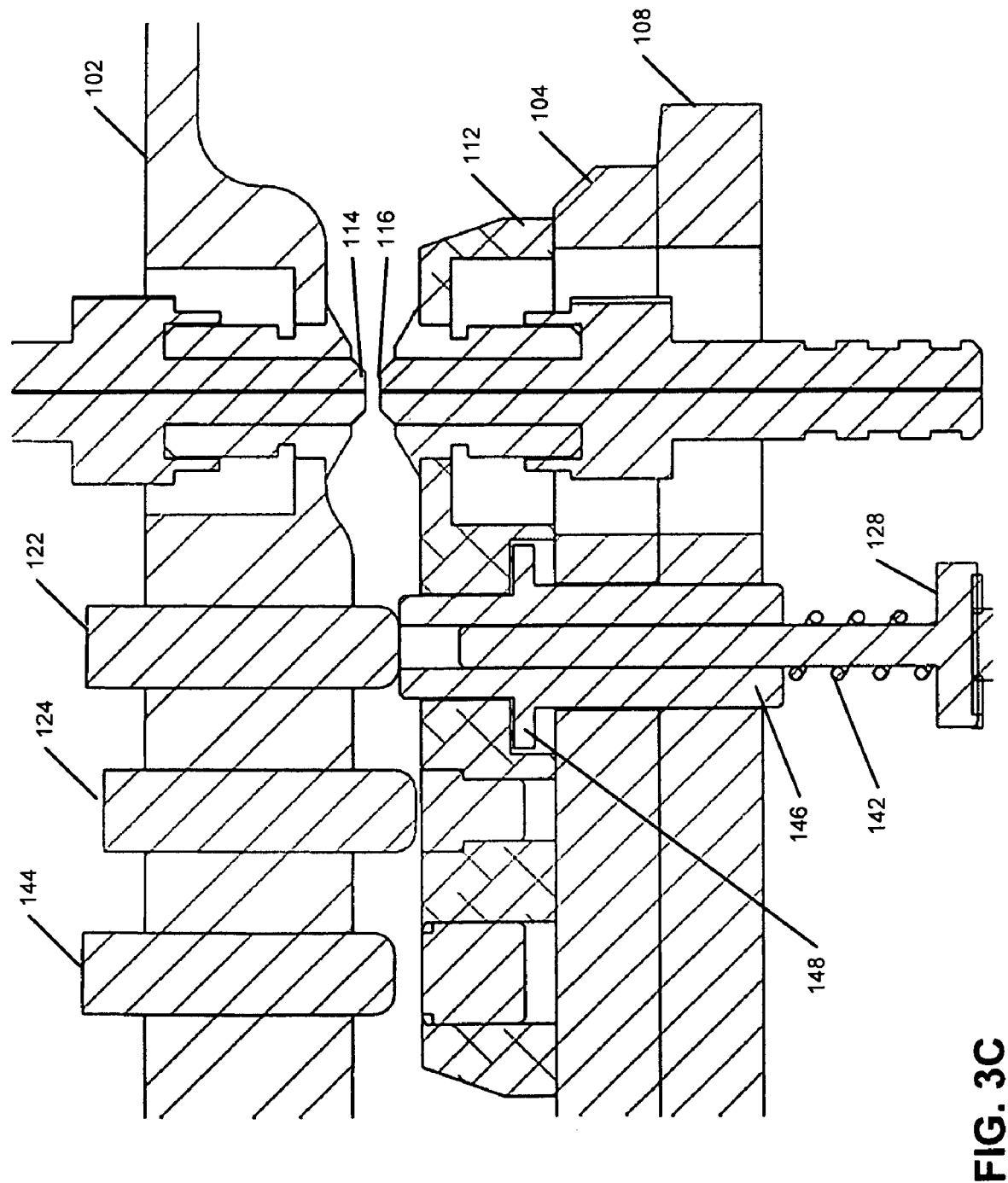

According to one embodiment, from the home position, the upper arm is positioned automatically by the actuator into a first measuring position as shown in FIGS. 3A-3C. Referring to FIGS. 3A-3C, from the home position, the pushing rod 126 is retreated by actuator 110 according to a preprogrammed procedure executed by a processor or controller. As shown in FIG. 3C, according to one embodiment, when the push rod 126 is moved downwardly, pushing pin 128 is pushed downwardly by spring 142 from a compressed state to a released state. As a result, the tip portion of the pushing pin 128 is retreated into the sliding tunnel of plunger 146. However, the pushing rod 126 of actuator 110 does not retreat all the way down. Instead, the pushing rod 126 stops at a predetermined position, such that although the tip portion of pushing pin 128 retreats into sliding tunnel of plunger 146, spring 142 is still compressed against the stop surface of pushing pin 128 and lower end of plunger 146. As a result, the stopping ring of plunger 146 is still pushed against the top inner wall of the internal room formed by the cutout of base platform 112 and the top surface of lower arm 104. Therefore, the tip portion of plunger 146 remains exposed external to the top surface of base platform 112, where pin 122 rests on the top surface of plunger 146 as shown in FIG. 3C.

At this position, upper arm 102 is positioned lower than the home position. The space between measuring surfaces 114 and 116 is approximately 1 mm and an optical measurement of the liquid sample may be performed at this measuring position (also referred to as a first measuring position). Note that at this measuring position, both measuring surfaces 114 and 116 are in contact with the liquid sample, creating an optical path as shown in FIG. 6D. Also note that at this measuring position, pin 124 is not in contact with the top surface of base platform 112, where the space between the lower end of pin 124 the top surface of base platform 112 is less than the space between the lower end of pin 122 and the top surface of base platform 112. The space between the lower end of pin 124 the top surface of base platform 112 is used to determine a second measuring position which will be described below.

After the first measurement has been made at the first measuring position as shown in FIGS. 3A-3C, the controller continues to perform according to the testing procedure which may be written in a computer programming language and stored in a machine readable storage medium such as a memory. Specifically, according to one embodiment, the controller controls the actuator 110 to retreat pushing rod downwardly as shown in FIGS. 4A-4C from the first measuring position described above as shown in FIGS. 3A-3C.

Figure 4A:
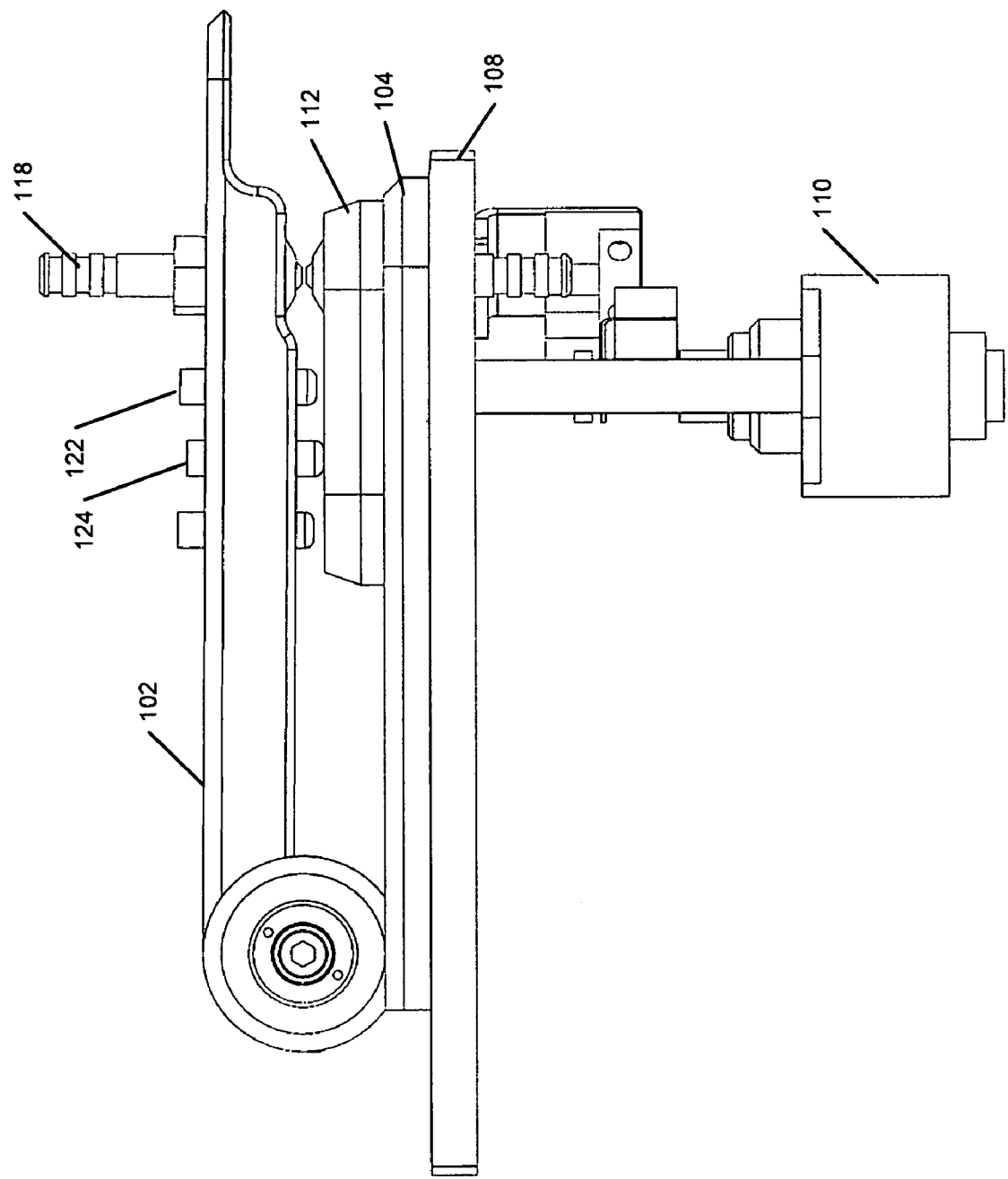
FIGS. 4A-4C show perspective views of an apparatus for measuring liquid sample according to one embodiment of the invention.
Figure 4B:
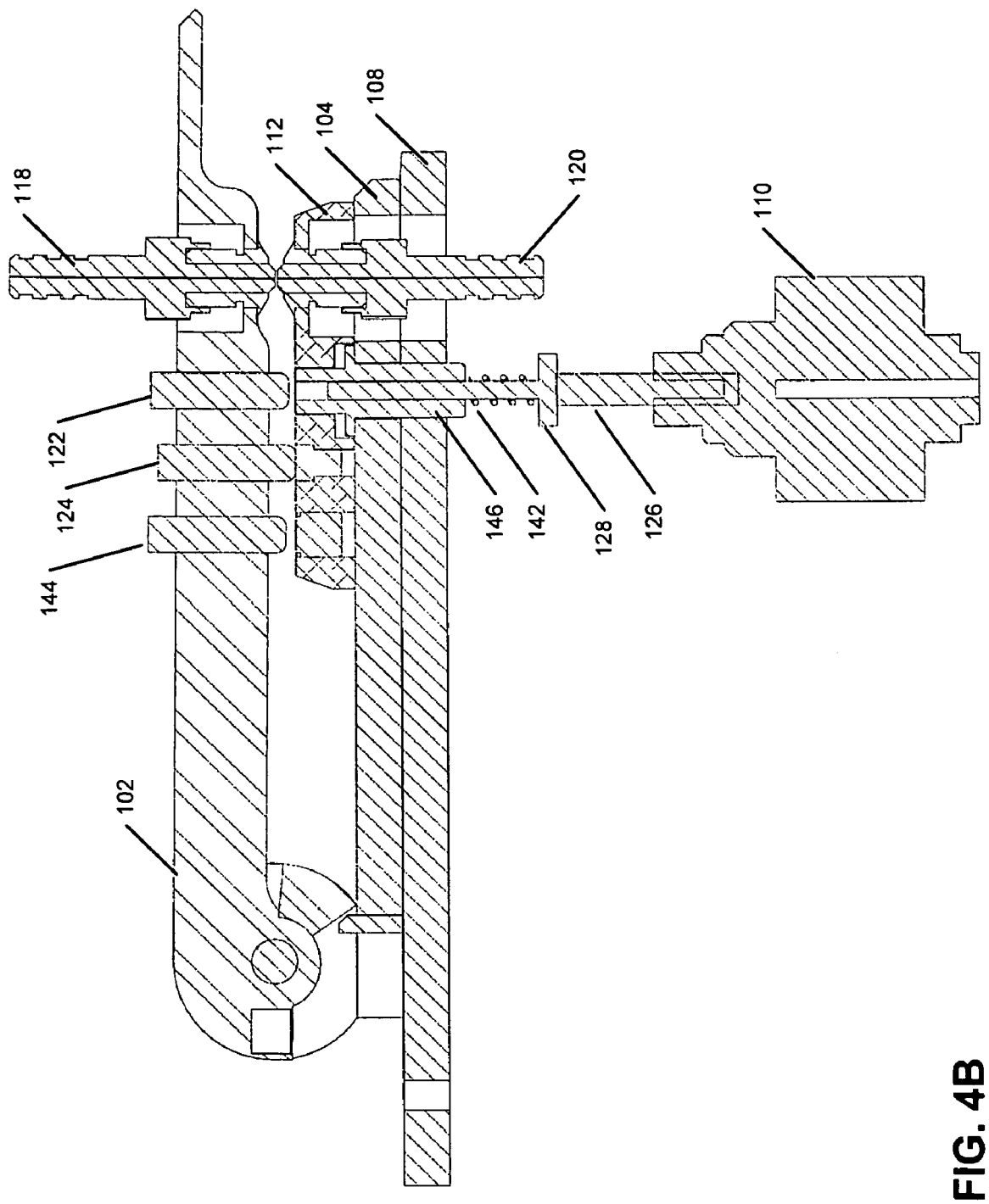
Figure 4C:
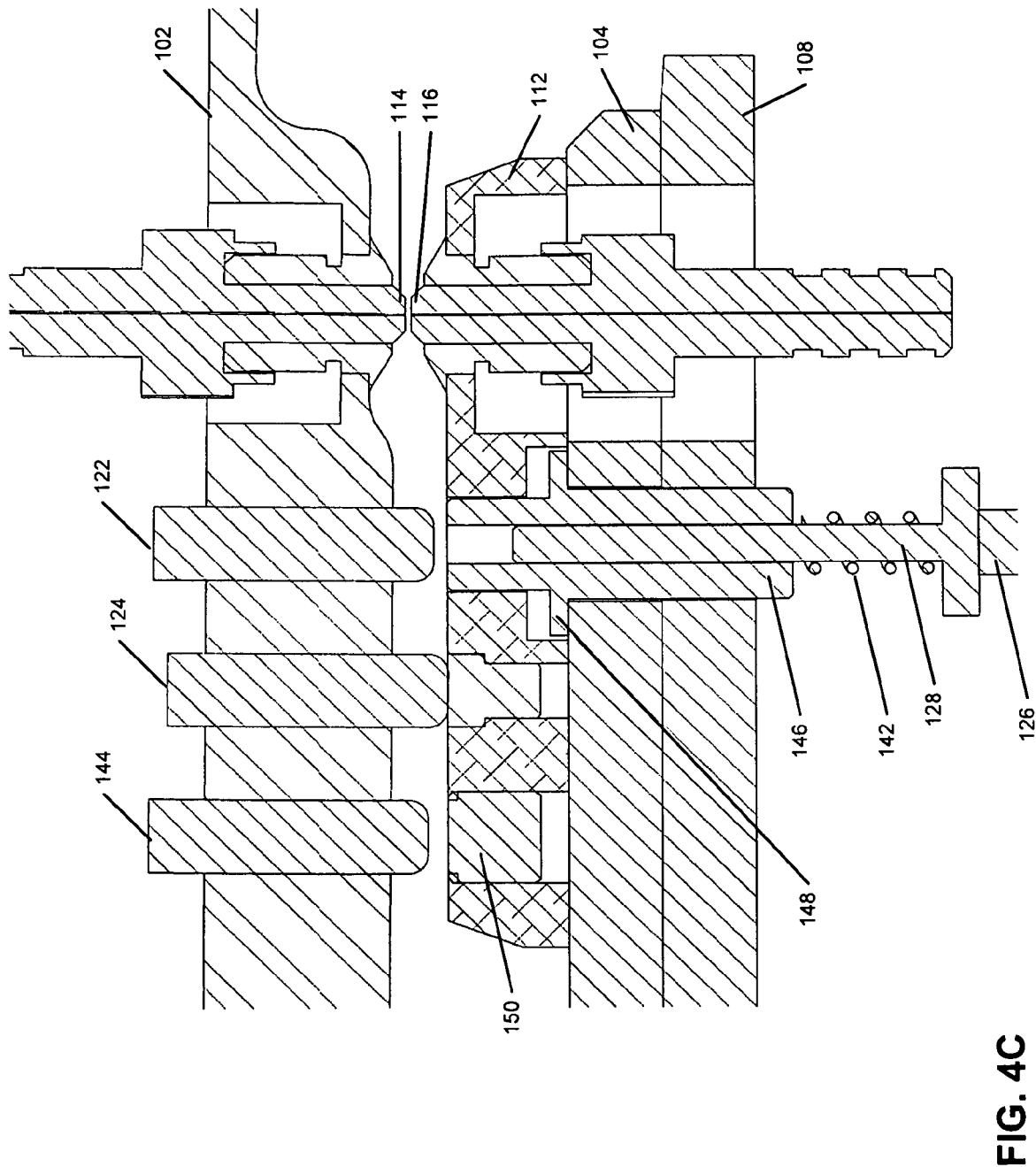

Referring to FIGS. 4A-4C, according to one embodiment, as the pushing rod 126 is moved down by the actuator 110, due to the gravity as well as the force generated from the compressed spring 142, pushing pin 128 also moves down. As the pushing pin 128 is moving down, the tip portion of pushing pin 128 is retreated into the sliding tunnel of plunger 146. As the pushing rod 126 and pushing pin 128 continue to move down, spring 142 is completely released and it no longer pushes the plunger 146 upwardly. As a result, due to the gravity, plunger 146 also moves down until the stopping ring 148 is stopped by the top surface of lower arm 104. In this situation, the tip portion of plunger 146 is no longer exposed beyond the top surface of base platform 112.

Due to the gravity as well as magnetic force generated from metal pin 144 and magnet 150, upper arm 102 is moved (e.g., "pulled") lower towards the lower arm 104. The upper arm 102 is moved lower until pin 124 reaches the top surface of base platform 112, in which case, the upper arm 102 rests on the lower arm 104 via pin 124. This position is referred to as a second measuring position and an optical measurement of the liquid sample can then be performed. At this measuring position, the space between measuring surfaces 114 and 116 is approximately 0.2 mm. The measuring surfaces 114 and 116 are also in contact with the liquid sample, maintaining the optical path as shown in FIG. 6D. Thereafter, the testing procedure may be completed.

Figure 7:
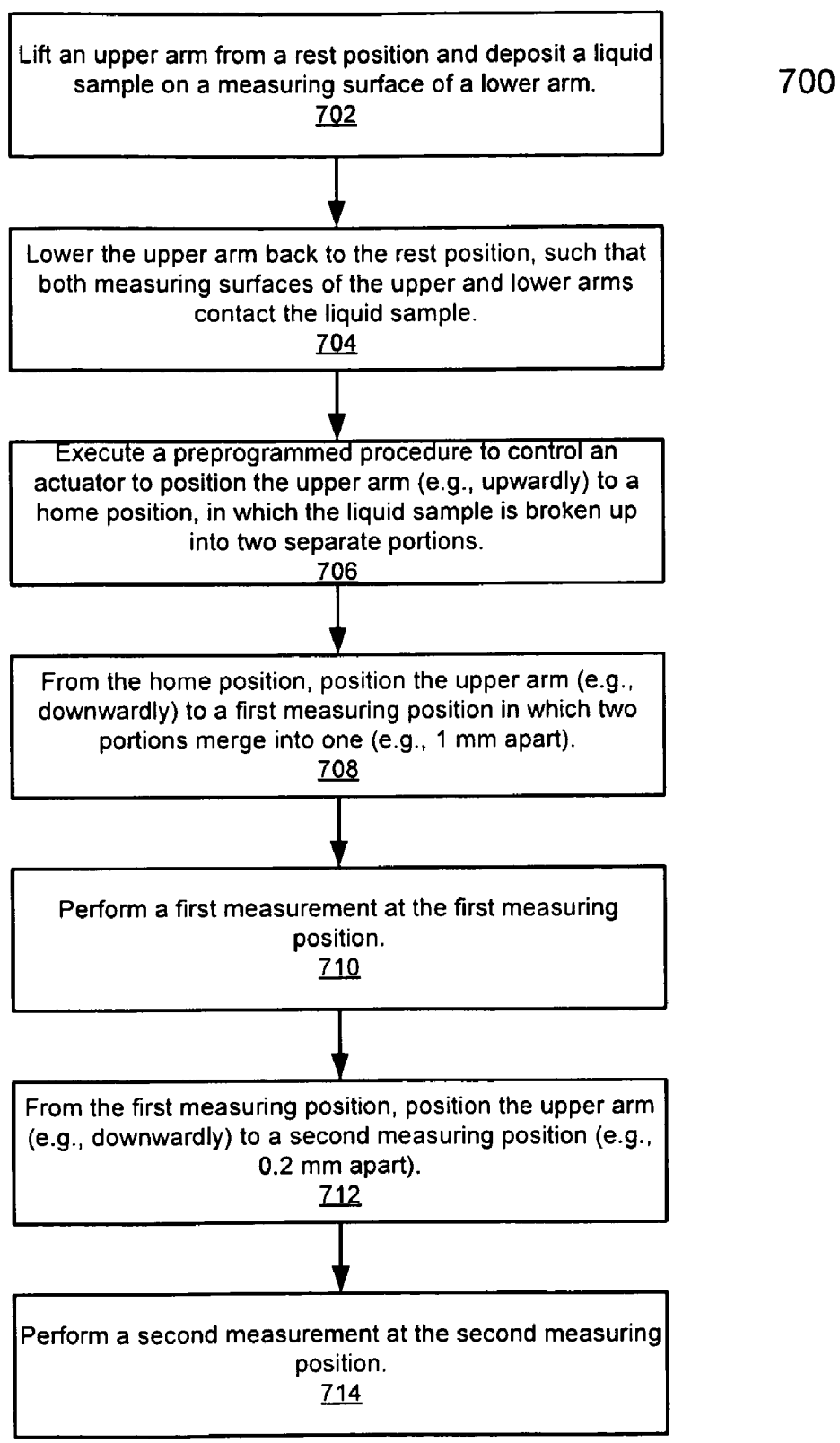
FIG. 7 is a flow diagram illustrating a process for measuring optical characteristics of a liquid samples according to one embodiment of the invention.

FIG. 7 is a flow diagram illustrating a process for measuring optical characteristics of a liquid sample according to one embodiment. Note that process 700 may be performed by processing logic which may include hardware, software, or a combination of both. For example, process 700 may be performed by an apparatus described above. Referring to FIG. 7, at block 702, an upper arm is lifted and a liquid sample to be measured is deposited onto a measuring surface of a lower arm, for example, as shown in FIG. 1B. At block 704, the upper arm is lowered back down to a rest position (e.g., FIG. 1C), such that both measuring surfaces of the upper and lower arms are in contact with the liquid sample.

From the rest position, at block 706, a preprogrammed procedure is executed, which may be programmed in a variety of programming languages and stored in a variety of machine-readable storage medium. Based on the preprogrammed procedure, an actuator is configured to position the upper arm to a home position (e.g., FIG. 2A) in which the liquid sample is broken up into two portions, one attached to a measuring surface of an upper arm and other attached to a measuring surface of a lower arm, where two portions are not in contact with each other.

From the home position, continuing with the preprogrammed procedure, at block 708, the actuator is configured to position the upper arm to a first measuring position (e.g., FIG. 3A) in which two portions of the liquid sample merge into one. As a result, an optical path is formed. As described above, the space between two measuring surfaces of the upper and lower arms is approximately 1 mm apart. At the first measuring position, at block 710, a first measurement is performed.

From the first measuring position, continuing with the preprogrammed procedure, at block 712, the actuator is configured to position the upper arm to a second measuring position (e.g., FIG. 4A). As described above, the space between two measuring surfaces of the upper and lower arms is approximately 0.2 mm apart. At the second measuring position, at block 714, a second measurement is performed. Other operations may also be performed.

As described above, although an apparatus as described above in several embodiments of the invention can be configured in two measuring positions in which two measurements of light absorption of a liquids sample can be made; however, it is not so limited, more or fewer measuring positions may also be configured, dependent upon specific circumstances. In addition, although an apparatus can be configured in multiple measuring positions, it is not necessary to conduct multiple measurements during the experiment. Fewer or more measurements than measuring positions may be conducted.

For example, according to one embodiment, after the first measurement has been made at the first measuring position, if it is determined that the first measurement has satisfied a predetermined criteria, the second measurement may be skipped even though the apparatus can be programmed for multiple measuring positions. However, according to an alternative embodiment, if the first measurement is not good enough (e.g., certain optical characteristics of a liquid sample cannot be obtained), the apparatus may then be positioned in a second measuring position and a second measurement may be conducted.

Furthermore, as described above, the second measuring position as shown in FIGS. 4A-4C may be substantially the same as the rest position as shown in FIG. 1C. Thus, at the rest position, a first measuring may be performed. If the first measurement is good enough, the measuring procedure may end. However, if the first measurement performed at the rest position is not good enough, the measuring procedure may proceed to configure the apparatus to the home position as shown in FIGS. 2A-2C and then to the first measuring position as shown in FIGS. 3A-3C, upon which a second measurement is performed.

Thus, the apparatus as described above supports multiple measuring positions and dependent upon certain configurations, such measuring positions can be adjusted by either adjusting the positions of pins 122 and 124, or alternatively, by modifying the computer program that controls the controller which in turn controls the actuator. Such adjustments may be made dependent upon characteristics such as density of the liquid samples. Other configurations may exist.

Figure 8:
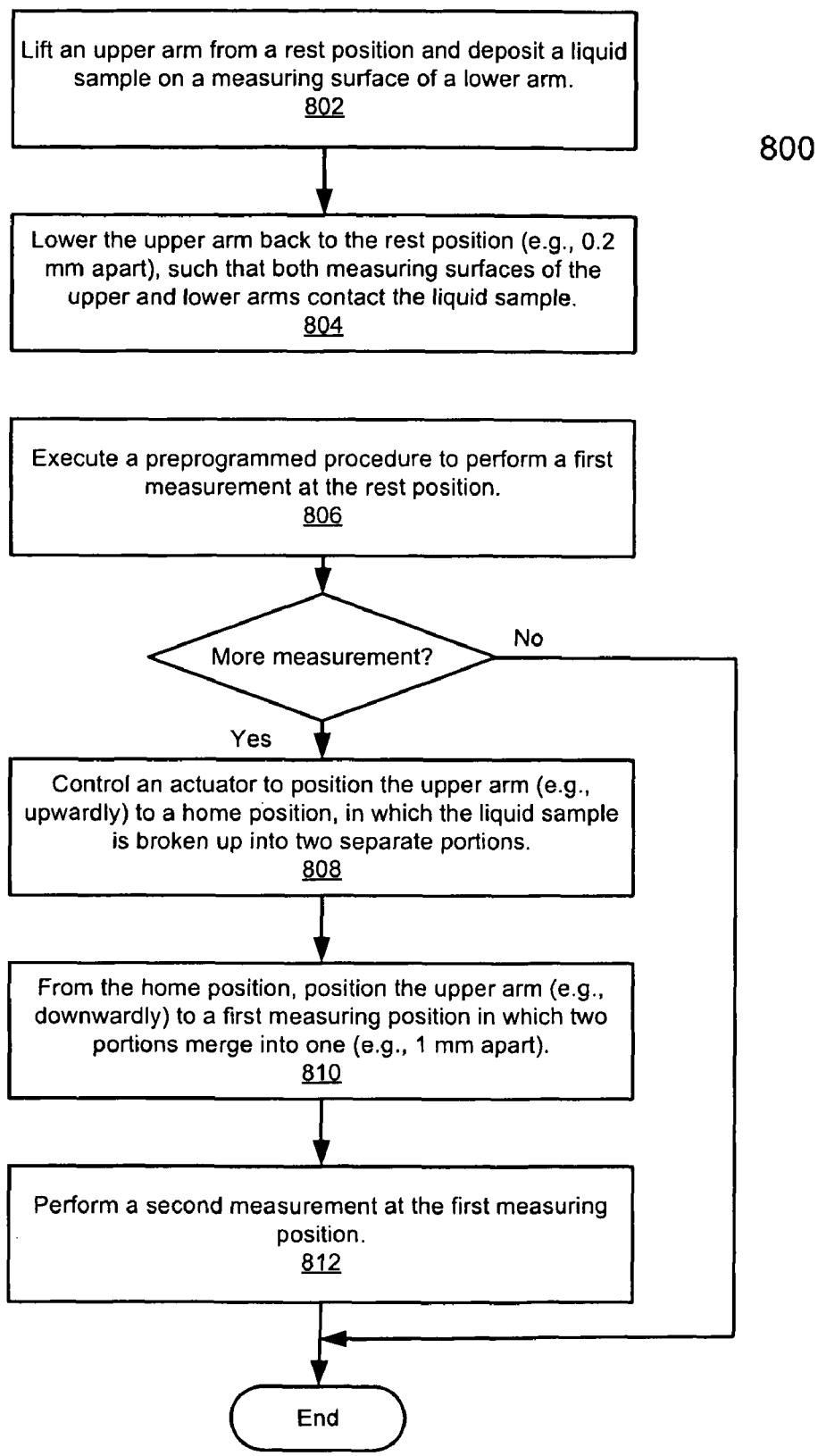
FIG. 8 is a flow diagram illustrating a process for measuring optical characteristics of a liquid samples according to another embodiment of the invention.

FIG. 8 is a flow diagram illustrating a process for measuring optical characteristics of a liquid sample according to another embodiment. Note that process 800 may be performed by processing logic which may include hardware, software, or a combination of both. For example, process 800 may be performed by an apparatus described above. Referring to FIG. 8, at block 802, an upper arm is lifted and a liquid sample to be measured is deposited onto a measuring surface of a lower arm, for example, as shown in FIG. 1B. At block 804, the upper arm is lowered back down to a rest position (e.g., FIG. 1C), such that both measuring surfaces of the upper and lower arms are in contact with the liquid sample, forming an optical path.

From the rest position, at block 806, a preprogrammed procedure is executed, which may be programmed in a variety of programming languages and stored in a variety of machine-readable storage medium. As described above, due to the gravity and the magnetic field generated from between a metal piece of the upper arm and a magnet embedded within the lower arm, the space between measuring surfaces of the upper and lower arms is approximately 0.2 mm apart. Based on the preprogrammed procedure, a first measurement is performed at the rest position.

Based on a measurement result of the first measurement, it is determined whether an additional measurement is needed. If an additional measurement is not needed, process 800 is terminated. However, if an additional measurement is needed, at block 808, from the rest position, an actuator is configured to position the upper arm to a home position (e.g., FIG. 2A) in which the liquid sample is broken up into two portions, one attached to a measuring surface of an upper arm and other attached to a measuring surface of a lower arm, where two portions are not in contact with each other.

From the home position, continuing with the preprogrammed procedure, at block 810, the actuator is configured to position the upper arm to a first measuring position (e.g., FIG. 3A) in which two portions of the liquid sample merge into one. As a result, an optical path is formed again. As described above, the space between two measuring surfaces of the upper and lower arms is approximately 1 mm apart. At the first measuring position, at block 812, a second measurement is performed. Other operations may also be performed.

Note that the above description and drawings regarding embodiments of the invention are described for purposes of illustration only. Alternative designs and structures may also be implemented. For example, referring to FIGS. 2A-2C, according to an alternative embodiment, measuring platform 112 may be optional. That is, platform 112 may be omitted, while lower arm 104 may also serve as a part of measuring platform, having similar functionality as platform 112.

For example, measuring surface 116 may be directly disposed on a top surface of lower arm 104. The lower arm 104 includes a cutout disposed on a bottom surface of the lower arm, which when attached together with a top surface of base 108, forms a room for enclosing stop ring 148. That is, the stop ring 148 is disposed in the room enclosed by a bottom surface of lower arm 104 and a top surface of base 108. Magnet 150 is embedded within the lower arm 104. Other configurations may also exist.

Figure 9:
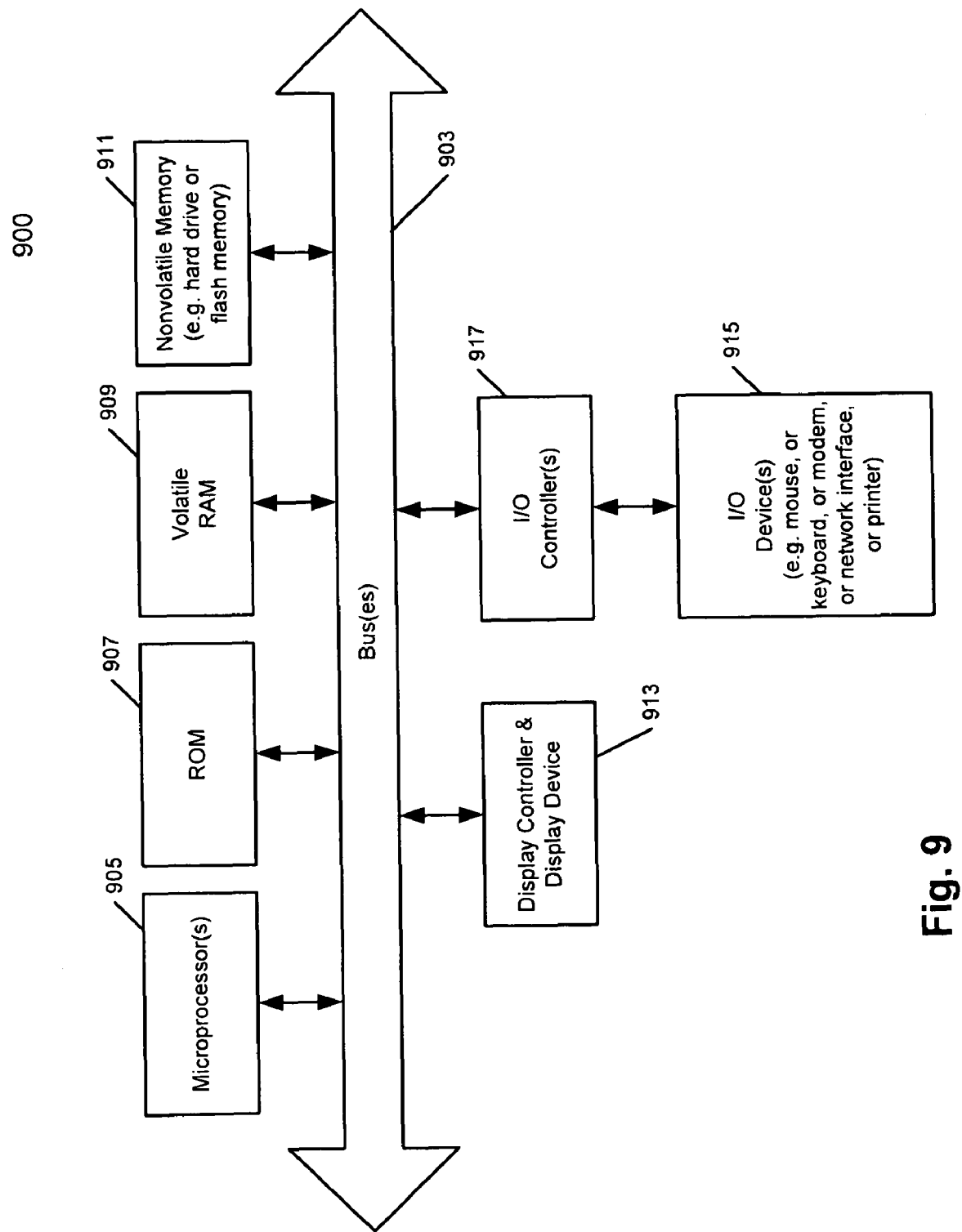
FIG. 9 is a block diagram illustrating a data processing system which may be used with an embodiment of the invention.

FIG. 9 shows one example of a data processing system 900 which may be used with one embodiment the invention. For example, the system 900 may be implemented as a part of a computer or controller that controls an actuator or optical sensor described above. Note that while FIG. 9 illustrates various components of a computer system, it is not intended to represent any particular architecture or manner of interconnecting the components as such details are not germane to the present invention. It will also be appreciated that network computers and other data processing systems which have fewer components or perhaps more components may also be used with the present invention.

As shown in FIG. 9, the computer system 900, which is a form of a data processing system, includes a bus 903 which is coupled to one or more microprocessors 905 and a ROM (Read Only Memory) 907 and volatile RAM 909 and a nonvolatile memory 911. The microprocessor 905 may retrieve the instructions from the memories 907, 909, 911 and execute the instructions to perform operations described above. The bus 903 interconnects these various components together and also interconnects these components 905, 907, 909, and 911 to a display controller and display device 913 and to peripheral devices such as input/output (I/O) devices which may be mice, keyboards, modems, network interfaces, printers and other devices which are well known in the art. Typically, the input/output devices 915 are coupled to the system through input/output controllers 917. The volatile RAM (random access memory) 909 is typically implemented as dynamic RAM (DRAM) which requires power continually in order to refresh or maintain the data in the memory.

The mass storage 911 is typically a magnetic hard drive or a magnetic optical drive or an optical drive or a DVD RAM or a flash memory or other types of memory systems which maintain data (e.g. large amounts of data) even after power is removed from the system. Typically, the mass storage 911 will also be a random access memory although this is not required. While FIG. 9 shows that the mass storage 911 is a local device coupled directly to the rest of the components in the data processing system, it will be appreciated that the present invention may utilize a non-volatile memory which is remote from the system, such as a network storage device which is coupled to the data processing system through a network interface such as a modem, an Ethernet interface or a wireless network. The bus 903 may include one or more buses connected to each other through various bridges, controllers and/or adapters as is well known in the art.

Thus, techniques for measuring light absorption of liquid samples have been described herein. Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the required purposes, or it may comprise a general-purpose computer selectively activated or reconfigured by a computer program stored in the computer. Such a computer program may be stored in a computer readable medium. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., carrier waves, infrared signals, digital signals, etc.)), etc.

The algorithms and displays presented herein are not inherently related to any particular computer or other apparatus. Various general-purpose systems may be used with programs in accordance with the teachings herein, or it may prove convenient to construct more specialized apparatus to perform the required method operations. The required structure for a variety of these systems will appear from the description above. In addition, embodiments of the present invention are not described with reference to any particular programming language. It will be appreciated that a variety of programming languages may be used to implement the teachings of embodiments of the invention as described herein.

In the foregoing specification, embodiments of the invention have been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. An apparatus for measuring optical characteristics of liquid samples, the apparatus comprising:
   an upper arm having a first measuring surface;
   a lower arm having a second measuring surface, the upper arm coupled to the lower arm via a hinge and the upper arm capable of swinging relative to the lower arm via the hinge, wherein one of the first and second measuring surfaces is coupled to a light source while the other of the first and second measuring surface is coupled to a detector;
   an actuator configured to position the upper arm into a first measuring position with respect to the lower arm, wherein the first measuring surface of the upper arm and the second measuring surface of the lower arm are spaced approximately to contact and sandwich a liquid sample in between to form an optical path, such that light generated from the light source is received and detected through the light path by the detector for measuring light absorption by the liquid sample; and
   a controller coupled to the actuator, the controller executing a preprogrammed procedure to control the actuator to position the upper arm into the first measuring position,
   wherein prior to positioning the upper arm into a first measuring position by the actuator controlled by the controller, the upper arm is lifted such that the liquid sample can be deposited onto the second measuring surface of the lower arm, and wherein after the liquid sample has been deposited, the upper arm is lowered and rests on the lower arm in a rest position in which the first and second measuring surfaces are in contact with the liquid sample, and
   wherein from the rest position, the actuator is programmed to move the upper arm upwardly to a home position such that the liquid sample is broken up into a first part and a second part, the first part being attached to the first measuring surface of the upper arm while the second part being attached to the second measuring surface of the lower arm.

2. The apparatus of claim 1, wherein when the upper arm is in the home position, a space between the first measuring surface of the upper arm and the second measuring surface of the lower arm is approximately 2 millimeters.

3. The apparatus of claim 1, wherein from the home position, the actuator is programmed to move the upper arm lower into the first measuring position, such that the first part and the second part of the liquid sample contact with each other merging into a single liquid sample, forming the optical path, in which a first measurement can be performed.

4. The apparatus of claim 3, wherein when the upper arm is in the first measuring position, a space between the first measuring surface of the upper arm and the second measuring surface of the lower arm is approximately 1 millimeter.

5. The apparatus of claim 3, wherein from the first measuring position, the actuator is programmed to move the upper arm further lower into a second measuring position, in which a second measurement can be performed.

6. The apparatus of claim 5, wherein when the upper arm is in the second measuring position, a space between the first measuring surface of the upper arm and the second measuring surface of the lower arm is approximately 0.2 millimeters.

7. The apparatus of claim 5, wherein the actuator is mounted underneath the lower arm, wherein the actuator includes a step motor and a pushing rod moving up and down in response to rotations of the step motor, wherein the pushing rod is moved up and down through a first tunnel of the lower arm and is configured to push the upper arm upwardly in response to a forward direction of the step motor, and wherein in response to a reversed direction of the step motor, the pushing rod retreats downwardly within the first tunnel such that the upper arm is lowered following the pushing rod due to gravity.

8. The apparatus of claim 7, further comprising:
a first pin disposed on a bottom surface of the upper arm; and
a second pin disposed on the bottom surface of the upper arm,
wherein when the pushing rod is pushed upwardly, the pushing rod pushes the first pin up which carries the upper arm upwardly into the home position, and wherein when the pushing rod is retreated completely into the first tunnel of the lower arm, the upper arm is moved lower due to gravity and rests via the second pin on the lower arm transitioning into the second measuring position.

9. The apparatus of claim 8, further comprising:
a plunger inserted into the first tunnel of the lower arm, the plunger capable of sliding up and down within the first tunnel, and the plunger having a second tunnel embedded therein; and
a pushing pin having an elongate body and a stop surface attached to one end of the elongate body, wherein the elongate body is inserted into the second tunnel of the plunger, the elongate body capable of sliding up and down within the second tunnel of the plunger,
wherein when the upper arm is positioned at the home position, the pushing rod pushes the pushing pin and the plunger up, such that a tip portion of the plunger is exposed beyond a top surface of the lower arm while a tip portion of the pushing pin is exposed beyond the tip portion of the plunger, supporting the upper arm.

10. The apparatus of claim 9, wherein when the upper arm is positioned at the first measuring position, the pushing rod and the pushing pin retreat such that the tip portion of the pushing pin retreats within the second tunnel of the plunger, while the tip portion of the plunger remains exposed beyond the top surface of the lower arm, supporting the upper arm.

11. The apparatus of claim 10, wherein when the upper arm is positioned at the second measuring position, the pushing rod retreats further down such that the plunger retreats within the first tunnel of the lower arm, and wherein the upper arm rests onto the lower arm supported via the second pin of the upper arm.

12. The apparatus of claim 11, further comprising:
a base measuring platform mounted on the top surface of the lower arm, wherein the second measuring surface is mounted on a top surface of the base measuring platform and the upper arm is supported on the top surface of the base measuring platform via one of the first and second pins mounted on the upper arm,
wherein the base measuring platform includes a third tunnel aligned with the first tunnel of the lower arm to allow the pushing pin to slide through both the first tunnel of the lower arm and the third tunnel of the base measuring platform in order to support the upper arm.

13. The apparatus of claim 12, wherein a lower end of the third tunnel includes a cutout having a diameter larger than a diameter of the third tunnel, wherein the plunger includes a stop ring having a diameter larger than a diameter of the plunger, wherein the cutout of the base measuring platform and the top surface of the lower arm form an internal room housing the stop ring of the plunger, and wherein a vertical space within the internal room to allow the stop ring of the plunger determines an amount of the tip portion of the plunger that can be moved up beyond the top surface of the base measuring platform.

14. The apparatus of claim 9, further comprising:
a U-shape positioning sensing piece mounted fixedly with respect to the lower arm, the U-shape positioning sensing piece having a first terminal and a second terminal, the first terminal including a light source transmitting light and the second terminal including an optical sensor to receive the light; and
a positioning blocking piece mounted on the pushing rod of the actuator, wherein when the pushing rod is moved upwardly, the positioning blocking piece also moves up and enters into an opening space between the first and second terminals of the U-shape positioning sensing piece thereby blocking the light transmitted and sensed between the first and second terminals, which determines the home position.

15. A method for measuring optical characteristics of liquid samples, the method comprising:
coupling one of an upper arm having a first measuring surface and a lower arm having a second measuring surface to a light source and coupling the other one of the upper arm and lower arm to an optical sensor to receive light transmitted from the light source;
lifting the upper arm such that the liquid sample can be deposited onto the second measuring surface of the lower arm;
lowering the upper arm to rest on the lower arm in a rest position in which the first and second measuring surfaces are in contact with the liquid sample;
operating an actuator, according to a preprogrammed procedure, to move the upper arm upwardly to a home position such that the liquid sample is broken up into a first part and a second part, the first part being attached to the first measuring surface of the upper arm while the second part being attached to the second measuring surface of the lower arm, and to position the upper arm into a first measuring position with respect to the lower arm, wherein the first measuring surface of the upper arm and the second measuring surface of the lower arm are spaced approximately to contact and sandwich a liquid sample in between to form an optical path, such that light generated from the light source is received and detected through the light path by the detector for measuring light absorption by the liquid sample.

16. The method of claim 15, further comprising, from the home position, the actuator moving the upper arm lower into the first measuring position, such that the first part and the second part of the liquid sample contact with each other merging into a single liquid sample, forming the optical path, in which a first measurement can be performed.

17. The apparatus of claim 15, wherein when the upper arm is in the home position, a space between the first measuring surface of the upper arm and the second measuring surface of the lower arm is approximately 2 millimeters.

18. The apparatus of claim 15, wherein from the home position, the actuator is programmed to move the upper arm lower into the first measuring position, such that the first part and the second part of the liquid sample contact with each other merging into a single liquid sample, forming the optical path, in which a first measurement can be performed.

19. The apparatus of claim 18, wherein from the first measuring position, the actuator is programmed to move the upper arm further lower into a second measuring position, in which a second measurement can be performed.

20. The apparatus of claim 19, wherein when the upper arm is in the first measuring position, a space between the first measuring surface of the upper arm and the second measuring surface of the lower arm is approximately 1 millimeter, and wherein when the upper arm is in the second measuring position, a space between the first measuring surface of the upper arm and the second measuring surface of the lower arm is approximately 0.2 millimeters.

* * * * *